(12) United States Patent
Poliakoff et al.

(10) Patent No.: US 7,238,804 B2
(45) Date of Patent: Jul. 3, 2007

(54) PREPARATION OF LACTAMS

(75) Inventors: Martyn Poliakoff, Nottingham (GB); Paul Hamley, Nottingham (GB); Chong Yan, Nottingham (GB); Eduardo Garcia-Verdugo Cepeda, Castellon (ES); Graham Robert Aird, County Durham (GB); Alexander Stuart Coote, Cleveland (GB); Ian Pearson, Cleveland (GB); William Barry Thomas, Cleveland (GB)

(73) Assignee: Invista North America S. AR. L., Wilmington, DE (US)

( * ) Notice: Subject to any disclaimer, the term of this patent is extended or adjusted under 35 U.S.C. 154(b) by 0 days.

(21) Appl. No.: 11/314,586

(22) Filed: Dec. 21, 2005

(65) Prior Publication Data

US 2006/0161000 A1    Jul. 20, 2006

Related U.S. Application Data

(60) Provisional application No. 60/645,219, filed on Jan. 18, 2005.

(51) Int. Cl.
*C07D 201/08*     (2006.01)

(52) U.S. Cl. ...................................................... 540/539
(58) Field of Classification Search ................. 540/539
See application file for complete search history.

(56) References Cited

U.S. PATENT DOCUMENTS 2,301,964 A    11/1942    Elmore
2,357,484 A     9/1944    Elmore

FOREIGN PATENT DOCUMENTS

WO    WO 02/076943    10/2002

OTHER PUBLICATIONS

Kramer et al, "Hydrolysis of Nitriles in Supercritical Water", Chem. Eng. Technol. 21, 1988, pp. 494-500.

*Primary Examiner*—Bruck Kifle

(57) ABSTRACT

A process for the manufacture of a lactam from an amino alkane nitrile and/or its hydrolysis derivatives, comprising reacting a solution comprising at least about 5% by weight amino alkane nitrile in water at a temperature of greater than or equal to about 350° C. and at a pressure of greater than about 250 bar. Optionally, a dilute acid may be added as a catalyst.

20 Claims, 1 Drawing Sheet

Effect of temperature at 350 bar

Temperature C

PREPARATION OF LACTAMS

CROSS-REFERENCE TO RELATED APPLICATION

This application claims benefit of priority from Provisional Application No. 60/645,219 filed Jan. 18, 2005.

FIELD OF THE INVENTION

The present invention relates to the production of lactams from amino alkane nitriles. In particular, the present invention relates to the production of epsilon-caprolactam ($\epsilon$-caprolactam) from 6-aminocapronitrile.

BACKGROUND OF THE INVENTION

Epsilon-caprolactam ($\epsilon$-caprolactam) is the main precursor for the preparation of nylon-6. Typically, industrial production processes for $\epsilon$-caprolactam are multistep and produce ammonium sulfate or other by-products. Currently, approximately 95% of the world's $\epsilon$-caprolactam is produced from cyclohexanone oxime via the Beckmann rearrangement.

A precursor material for cyclohexanone oxime is cyclohexanone. Precursor materials for cyclohexanone can include cyclohexane, phenol, and benzene. Accordingly, the first step (or steps) in the production of $\epsilon$-caprolactam is often a series of reductions and oxidations to form cyclohexanone from cyclohexane, phenol, or benzene. Cyclohexanone thus produced is next reacted with a hydroxylamine salt, usually the sulfate, to form cyclohexanone oxime and ammonium sulfate. The oxime is then rearranged in concentrated sulfuric acid, and the resulting lactam sulfate salt is hydrolyzed to form $\epsilon$-caprolactam and additional ammonium sulfate.

An alternative route to produce $\epsilon$-caprolactam is from adiponitrile via 6-aminocapronitrile (ACN). This cyclization of 6-aminocapronitrile can be conducted in the liquid or gas phase, with or without a catalyst. In this regard, U.S. Pat. No. 2,301,964 discloses a liquid phase cyclization of 6-aminocapronitrile at a temperatures of less than 380° C. and at reaction times of greater than 1 hour. U.S. Pat. No. 2,357,484, in turn, discloses a vapor phase process, having a short reaction time at temperatures between 150° C. and 500° C. Both processes use solid acid catalysts, which are prone to fouling, leading to increased operating and maintenance costs, as well as process downtime.

A. Krämer and H. Vogel., *Chem. Eng. Technol.* 21, 494-500 (1999) ("Krämer and Vogel")1 discloses a continuous hydrolysis of 6-aminocapronitrile in water to produce $\epsilon$-caprolactam at temperatures of between 250° C. and 350° C. and at a pressure of 250 bar. Using a feed comprising 5% by weight of 6-aminocapronitrile and the balance water, the authors demonstrated a 45% conversion of 6-aminocapronitrile and 55% selectivity towards $\epsilon$-caprolactam at a residence time of 100 seconds. Other work done in the 100 to 250 second residence time range indicates that increasing residence time increases conversion of 6-aminocapronitrile. In addition, the paper teaches that selectivity significantly decreases as reaction temperature increases beyond 380° C., and the data presented implies poor yields with this approach.

Methods for increasing the conversion of amino alkane nitrile with high selectivity to the corresponding lactam continue to be sought.

SUMMARY OF THE INVENTION

Accordingly, the present invention provides a process for producing a lactam from an amino alkane nitrile and/or its hydrolysis derivatives, comprising reacting a solution comprising about 5% by weight to about 80% by weight amino alkane nitrile in water at a temperature of greater than or equal to about 350° C. and up to about 480° C., and at a pressure of greater than about 250 bar and up to about 1000 bar. The molar ratio of the amino alkane nitrile to water is greater than about 1:1 mol/mol water to nitrile and less than about 100:1 mol/mol water to nitrile. Optionally, a dilute acid may be included as a catalyst.

DETAILED DESCRIPTION OF THE INVENTION

Figure 1:
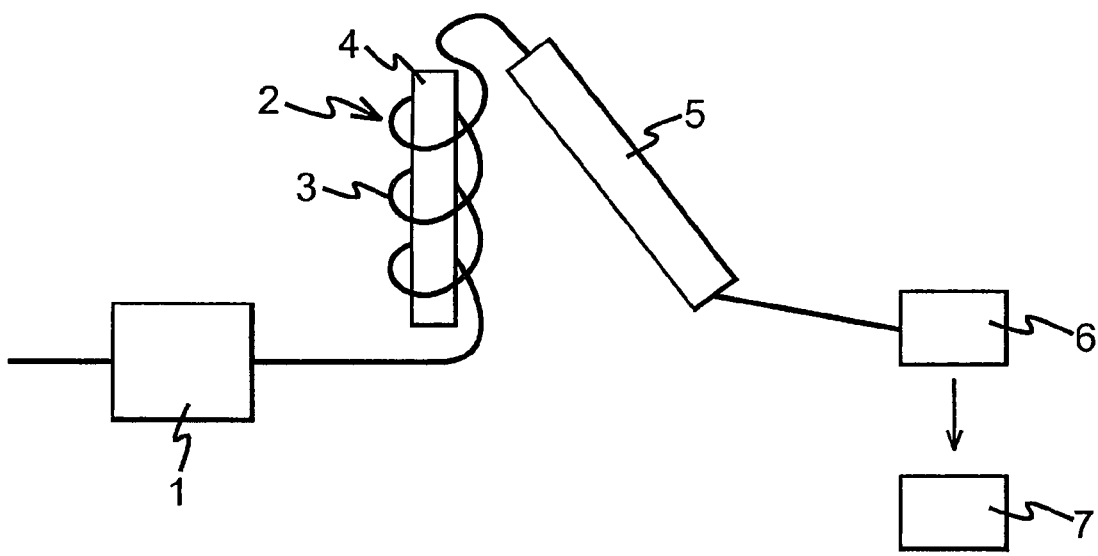
FIG. 1 is a schematic diagram of the experimental apparatus used according to the process of the invention.

The present invention provides a process for the manufacture of a lactam from an amino alkane nitrile and/or its hydrolysis derivatives (hydrolysis derivatives of amino alkane nitriles include amino amides and amino acids). In particular, the present invention relates to a process for producing a lactam at pressures above about 250 bar and at temperatures greater than or equal to about 350° C. At such pressures and temperatures, when a solution of amino alkane nitrile in water is reacted, high conversion of amino alkane nitrile and high selectivity to the corresponding lactam may be achieved.

Processes falling within the scope of the invention can be carried out under conditions in which water would be characterized as a supercritical fluid. A supercritical fluid is a substance above its critical temperature ($T_C$) and critical pressure ($P_C$). For a single component, the critical point represents the highest temperature and pressure at which the saturated substance can exist as a liquid and a vapour in equilibrium. At the critical point, the densities of the liquid and vapour phase coincide and the distinction between the two phases disappears. For water, the critical temperature is about 374° C. and the critical pressure is about 221 bar.

In the vicinity of the supercritical point, the physical properties of water change rapidly with temperature and pressure, including such properties as density, dielectric constant, dissociation constant, diffusion coefficient, and specific heat capacity. This effect can be utilized to alter the reaction regime of a number of chemical syntheses.

In processes of the invention, the pressure and temperature can be selected to secure supercritical or near critical conditions, based on the properties of pure water. In this regard, the temperature should be selected to be greater than or equal to about 350° C., such as greater than or equal to about 380° C., for example, greater than or equal to about 400° C. A typical range of operating temperatures can be, for example, about 350° C. to about 480° C., such as about 400° C. to about 450° C. Operating pressures should be greater than about 250 bar, such as from about 300 bar to about 1000 bar.

In certain embodiments, when the reaction temperature is between about 350° C. to about 400° C., such as from about 350° C. to about 380° C., the pressure can be maintained to be greater than or equal to about 350 bar and less than about 1000 bar. In other embodiments, pressures from about 260 bar to about 350 bar can yield satisfactory results.

Processes falling within the scope of the present invention can have the advantage of higher conversion of the amino alkane nitrile as well as greater selectivity to the corresponding lactam. As a consequence, while processes falling within the scope of the invention may optionally include a catalyst, they do not necessarily require one. When processes of the invention include a catalyst, a dilute acid may be used, such as, for example, a mineral or organic acid at a concentration of less then 10% by weight. Suitable acids include, but are not limited to, hydrochioric, sulphuric, alkyl or aromatic acids. Organic acids include, for example, acetic and benzoic acids.

The amino alkane nitrile to be converted in processes falling within the scope of the present invention has the general formula (I):

$$N{\equiv}C-R-NH_2 \qquad (I)$$

in which R is an alkyl group, which may be linear or branched, having from 3 to 20 carbon atoms. In at least one embodiment of the present invention, the amino alkane nitrile is 6-aminocapronitrile, and the corresponding lactam provided is ε-caprolactam.

Although the time period during which the amino alkane nitrile and water are to be maintained at the reaction temperature is not limited, the residence time may generally be short. For example, the residence time can be from about 10 seconds to about 4 minutes.

The concentration of amino alkane nitrile in the water should be at least about 5% by weight, based on the total weight of the solution. For the case of an aminocapronitrile, such as 6-aminocapronitrile, the concentration of nitrile in water can, for example, be from about 5% to about 80% by weight, based on the total weight of the solution. A concentration of at least 30%, based on the total weight of the solution, can also be used, and may be particularly suitable in certain industrial applications.

The molar ratio of water to amino alkane nitrile should be greater than 1:1 (as 1 mole of water is required per mole of aminocapronitrile for stoichiometric hydrolysis) and should be less than about 100:1.

In at least one embodiment, a process falling within the scope of the invention may be operated as a recycle operation in which the reaction mixture, including hydrolysis derivatives such as, but not limited to, amino amides, amino acids and linear polymers, after separation of the formed lactam, are returned to the reaction zone either alone or after mixing with fresh amino alkane nitrile. In such processes, the water is separated and recycled, as are the amino alkane nitrile starting material and hydrolysis derivatives. Any high boilers and ammonia can be purged, and the caprolactam can be separated and may be refined or used directly for subsequent conversion to nylon-6.

Processes falling within the scope of the present invention may involve reactions that are carried out adiabatically or isothermally. In addition, processes falling within the scope of the present invention may be operated continually in at least one continuous reactor. As used herein, "continuous reactor" means a reactor in which reactants are introduced and mixed and products withdrawn simultaneously in a continuous manner, as opposed to a batch-type reactor. For example, the reactor may be selected from a plug flow reactor, a stirred tank reactor, or a back-mixed reactor. However, the various aspects of the invention defined herein are not limited to any particular type of reactor. The present invention may be further illustrated by reference to the following non-limiting examples.

EXAMPLES

Examples falling within the scope of the present invention, as well as comparative examples, are listed in Table 1, with examples of the invention given a numerical designation (1-9) and comparative examples given an alphabetical designation (A-G). These examples were performed in a continuous tubular flow reactor, as described below (and illustrated schematically in FIG. 1).

The experimental parameters and results shown in Table 1 include selectivity, yield, percent conversion, and residence time. These parameters were determined as follows:

The selectivity ("% CPL Sel") of the product was calculated as:

$$\frac{\text{Product yield per pass} \times 100}{\text{Change in molar concentration of aminocapronitrile}}$$

where change in concentration of aminocapronitrile=the difference between aminocapronitrile concentration in the feed to the reactor and concentration of aminocapronitrile in the product stream.

The yield ("% CPL Yld" and "% dimer Yld") of product was calculated as:

$$\frac{\text{Analyzed molar concentration of product} \times 100}{\substack{\text{Aminocapronitrile molar concentration} \\ \text{in the feed to the reactor}}}$$

The aminocapronitrile conversion ("% ACN Con") was calculated as:

$$100 - \frac{\substack{\text{((analyzed molar concentration of} \\ \text{aminocapronitrile in product stream)} \times 100)}}{\substack{\text{aminocapronitrile molar concentration} \\ \text{in the feed to the reactor}}}$$

The residence times ("Res time") (the time at which the amino alkane nitrile and water are maintained at the reaction temperature) were calculated in seconds by dividing the volume of the reactor by the volumetric flow rate as follows:

$$\frac{\text{Volume of reactor (m}^3) \times \text{density at temperature (kg/m}^3)}{\text{Pump flow rate (m}^3/s) \times \text{density cold (kg/m}^3)}$$

The "density cold" was taken to be that of water at atmospheric temperature and pressure, the value used being 1000 kg/m³.

The density of the reaction fluid at a given temperature is an approximation. The density of pure water is well known and was determined for the reaction temperature and pressure using physical properties tables. Pure aminocapronitrile was treated as an ideal gas and the density determined accordingly. The reaction fluid density was then determined by calculating the weighted mean of the densities.

$$\left(\frac{\% \text{ of organic in feed}}{\text{Density of organic at temp and pressure}} + \frac{\text{Density of water at temp and pressure}}{100 - \% \text{ of organic in feed}}\right)$$

FIG. 1 is a schematic illustration of a continuous tubular flow reactor that was used to perform the examples of the invention as well as comparative examples. This type of reactor allowed assessment of the effect of the experimental conditions (e.g., temperature, pressure, residence time and ratio of organic constituent and water), providing for a rapid optimization of the process.

Referring to FIG. 1, a pump 1 supplied an aminocapronitrile solution from a feed system (not shown) to a reactor 2. The reactor 2 was a continuous tubular flow reactor, having a 20 m long pipe 3, having an outside diameter (OD) of about 0.16 cm (1/16 inch) and a wall thickness of about 0.05 cm (0.02 inch). Heating was provided by a block heater 4 inserted in a brass block, and lagged to retain heat. Cooling was accomplished by a water condenser 5, fabricated by placing a 30 cm length of 0.625 cm (1/4 inch) tubing around the 0.16 cm (1/16 inch) process tubing and passing water between the two. Cooling water flowed in the opposite direction to the process stream. Condenser 5 was positioned as close as possible to the exit point of reactor 2, to allow immediate quenching of the reaction mixture by heat exchange on exiting the reactor, and to allow an accurate calculation of residence time. The temperature exiting the condenser 5 was consistently maintained below about 25° C. Once cooled, the reactants passed through a backpressure regulator 6 (which controlled the pressure of the reaction) before reaching a sampling point 7. When desired, filters (not shown) were inserted between condenser 5 and backpressure regulator 6. Adjusting the mass throughput of the unit and the reactor length controlled the residence time of the experiments.

Examples 1-9 are examples of processes according to the present invention, wherein the % ACN, Flow rate, Temperature, Pressure, and Residence time are as shown in Table 1. Examples A-G of Table 1 are Comparative Examples. Comparative Example A is a simulation of the conditions of Krämer and Vogel and demonstrates similar yields and selectivities as reported therein. Comparative Examples B & C demonstrate the observation of Krämer and Vogel that simply increasing the temperature above 380° C. at 250 bar decreases the selectivity to the lactam. Example 1 demonstrates an embodiment of a process falling within the scope of the invention, whereby increasing the pressure above 250 bar has a positive impact on the process, and produces better conversion of the nitrile, and better selectivity to the lactam at temperatures greater than 380° C.

Example 1, as well as other examples of the invention, demonstrate that increasing the pressure increases the conversion of the nitrile and the yield to the lactam. Furthermore, increasing the temperature from 350° C. to 400° C. increases the nitrile conversion, and the yield and selectivity to the corresponding lactam. It also decreases dimer formation.

Figure 2:
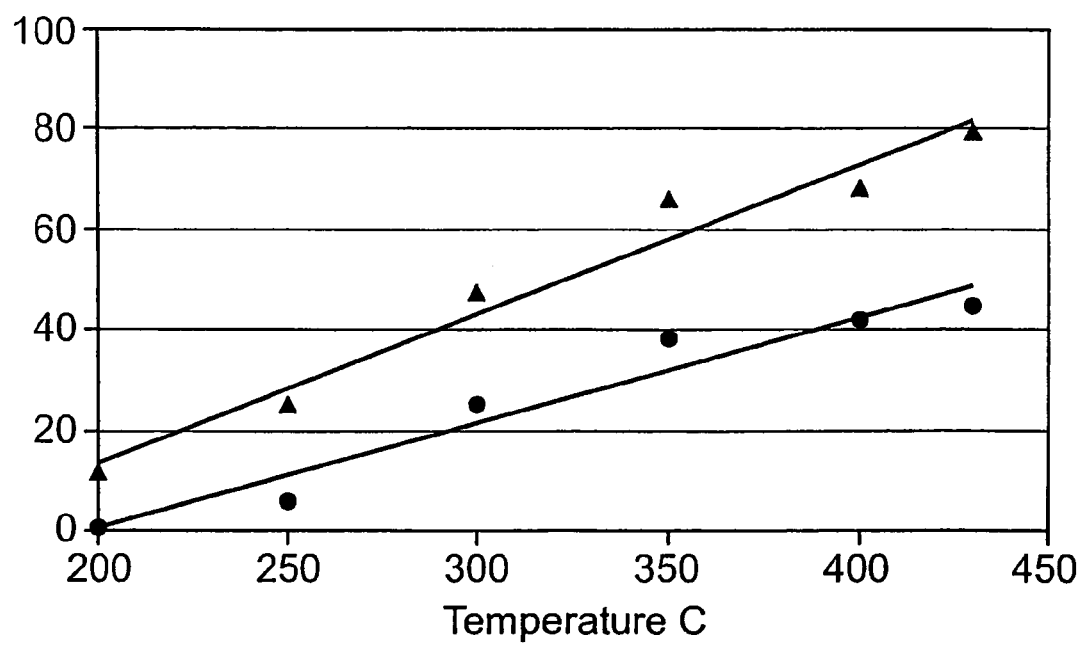
FIG. 2 is a plot that compares % ACN conversion (▲) and % caprolactam (CPL) yield (●) according to the results obtained in the Examples.

FIG. 2 plots the % ACN conversion (▲) and % caprolactam (CPL) yield (●) obtained in Examples 2, 3 and 9 and Comparative Examples E, F and G. It can be seen that ACN conversion and CPL yield both increase with increasing temperature at this higher pressure.

TABLE 1

| EX | % ACN | Flow rate (ml/min) | Temp (° C.) | Pressure (bar) | Res time (s) | % ACN Con | % CPL Yld | % CPL Sel | % dimer Yld |
|---|---|---|---|---|---|---|---|---|---|
| A | 5 | 2.2 | 350 | 250 | 102 | 47.2 | 30.3 | 64.4 | 0.3 |
| B | 30 | 1.5 | 350 | 250 | 154 | 49.6 | 29.5 | 59.5 | 3 |
| C | 30 | 1.5 | 400 | 250 | 51 | 28.27 | 13.60 | 48.11 | 0.96 |
| 1 | 5 | 1.5 | 400 | 350 | 114 | 67.3 | 54 | 80.2 | 0.5 |
| 2 | 30 | 1.5 | 400 | 350 | 127 | 68.1 | 41.8 | 61.4 | 4.0 |
| D | 30 | 1.5 | 200 | 200 | 207 | 11 | 0.4 | 3.6 | 0.03 |
| 3 | 30 | 1.5 | 350 | 350 | 160 | 66 | 38.2 | 58 | 4.6 |
| 4 | 30 | 1.5 | 350 | 375 | 161 | 84 | 47.6 | 56.7 | 3.9 |
| 5 | 30 | 1.5 | 400 | 375 | 127 | 93.2 | 58.2 | 62.4 | 1.5 |
| 6 | 30 | 1.5 | 430 | 375 | 96 | 93.4 | 61.1 | 65.5 | 1.4 |
| 7 | 30 | 1.5 | 350 | 300 | 157 | 57.8 | 33.9 | 58.7 | 4.29 |
| 8 | 30 | 1.5 | 400 | 300 | 98 | 46.7 | 29.7 | 62.9 | 2.95 |
| E | 30 | 1.5 | 200 | 350 | 208 | 11.59 | 0.52 | 4.5 | 0.09 |
| F | 30 | 1.5 | 250 | 350 | 195 | 25.07 | 5.89 | 23.5 | 0.86 |
| G | 30 | 1.5 | 300 | 350 | 180 | 47.44 | 24.99 | 52.68 | 3.43 |
| 9 | 30 | 1.5 | 430 | 350 | 91 | 79.5 | 44.78 | 56.29 | 1.6 |

Nothing in this specification should be considered as limiting the scope of the present invention. All examples presented are representative and non-limiting. The above described embodiments of the invention may be modified or varied, and elements added or omitted, without departing from the invention, as appreciated by persons skilled in the art in light of the above teachings. It is therefore to be understood that the invention is to be measured by the scope of the claims, and may be practiced in alternative manners to those which have been specifically described in the specification.

What is claimed is:

1. A process for producing a lactam, comprising reacting a solution comprising about 5% by weight to about 80% by weight of an amino alkane nitrile in water at a temperature of greater than or equal to about 350° C. up to a temperature of about 480° C. and at a pressure greater than about 250 bar up to a pressure of about 1000 bar, wherein the molar ratio of the amino alkane nitrile in water is greater than about 1:1 mol:mol water to nitrile and less than about 100:1 mol:mol water to nitrile.

2. The process according to claim 1, wherein the reactants are maintained at the reaction temperature for from about 10 seconds to about 4 minutes.

3. The process according to claim 1, wherein the alkyl group of the amino alkane nitrile has from 3 to 20 carbon atoms.

4. The process according to claim 2, wherein the alkyl group of the amino alkane nitrile has from 3 to 20 carbon atoms.

5. The process according to claim 3, wherein the lactam is ε-caprolactam and the amino alkane nitrile is 6-aminocapronitrile.

6. The process according to claim 4, wherein the lactam is ε-caprolactam and the amino alkane nitrile is 6-aminocapronitrile.

7. The process according to claim 1, wherein the solution comprises at least about 30% by weight of said amino alkane nitrile.

8. The process according to claim 1, wherein the pressure is from about 300 to about 1000 bar.

9. The process according to claim 1, further comprising reacting the solution in the presence of up to about 10% by weight of an acid.

10. The process according to claim 9, wherein the acid is selected from the group consisting of hydrochloric acid, sulphuric acid, alkyl acid, aromatic acid, acetic acid and benzoic acid.

11. A process for producing a lactam, comprising:
(a) reacting a solution comprising about 5% by weight to about 80% by weight of an amino alkane nitrile in water at a temperature of greater than or equal to about 350° C. up to a temperature of about 480° C. and at a pressure greater than about 250 bar up to a pressure of about 1000 bar, in a reactor, wherein the molar ratio of the amino alkane nitrile in water is greater than about 1:1 mol:mol water to nitrile and less than about 100:1 mol:mol water to nitrile, thereby producing said lactam and hydrolysis derivatives of the amino alkane nitrile;
(b) separating said lactam from said hydrolysis derivatives; and
(c) recycling said hydrolysis derivatives to said reactor; wherein said hydrolysis derivatives are at least one of amino amides, amino acids or linear polymers formed from said amino alkane nitrile during said reaction in said reactor.

12. The process according to claim 11, wherein the reactants are maintained at the reaction temperature for from about 10 seconds to about 4 minutes.

13. The process according to claim 11, wherein the alkyl group of the amino alkane nitrile has from 3 to 20 carbon atoms.

14. The process according to claim 13, wherein the lactam is ε-caprolactam and the amino alkane nitrile is 6-aminocapronitrile.

15. The process according to claim 11, wherein the solution comprises at least about 30% by weight of said amino alkane nitrile.

16. The process according to claim 11, wherein the pressure in said reactor is from about 300 to about 1000 bar.

17. The process according to claim 11, further comprising reacting the solution in the presence of up to about 10% by weight of an acid.

18. The process according to claim 17, wherein the acid is selected from the group consisting of hydrochloric acid, sulphuric acid, alkyl acid, aromatic acid, acetic acid and benzoic acid.

19. A process for producing a lactam, comprising reacting a solution comprising about 5% by weight to about 80% by weight of an amino alkane nitrile in water at a temperature of greater than or equal to about 350° C. up to a temperature of about 480° C. and at a pressure greater than about 250 bar up to a pressure of about 1000 bar, wherein the molar ratio of the amino alkane nitrile in water is greater than about 1:1 mol:mol water to nitrile and less than about 100:1 mol:mol water to nitrile, further wherein said amino alkane nitrile has the general formula (I)

$$N{\equiv}C{-}R{-}NH_2 \qquad (I)$$

in which R is an alkyl group, which may be linear or branched, having from 3 to 20 carbon atoms.

20. The process according to claim 19, further comprising reacting the solution in the presence of up to about 10% by weight of an acid selected from the group consisting of hydrochloric acid, sulphuric acid, alkyl acid, aromatic acid, acetic acid and benzoic acid.

* * * * *

UNITED STATES PATENT AND TRADEMARK OFFICE
CERTIFICATE OF CORRECTION

PATENT NO. : 7,238,804 B2
APPLICATION NO. : 11/314586
DATED : July 3, 2007
INVENTOR(S) : Poliakoff et al.

It is certified that error appears in the above-identified patent and that said Letters Patent is hereby corrected as shown below:

Column 5, lines 5 to 10, delete the formula and add the following:

-- [(% of organic in feed x density of organic at Temp. & Press.) + ((100 - % of org. in feed) x density of water at Temp. & Press.)] / 100 --

Signed and Sealed this

Thirtieth Day of October, 2007

JON W. DUDAS
*Director of the United States Patent and Trademark Office*